(12) United States Patent
Field

(10) Patent No.: US 7,726,315 B2
(45) Date of Patent: Jun. 1, 2010

(54) VALVES

(75) Inventor: Stephen James Field, Canterbury (GB)

(73) Assignee: Smiths Group PLC, London (GB)

( * ) Notice: Subject to any disclaimer, the term of this patent is extended or adjusted under 35 U.S.C. 154(b) by 1234 days.

(21) Appl. No.: 10/680,110

(22) Filed: Oct. 8, 2003

(65) Prior Publication Data

US 2004/0082923 A1   Apr. 29, 2004

(30) Foreign Application Priority Data

Oct. 29, 2002   (GB)   ................... 0225075.1

(51) Int. Cl.
*A61M 16/20* (2006.01)
*A61M 16/00* (2006.01)
*A61M 16/04* (2006.01)

(52) U.S. Cl. ............... 128/207.16; 128/205.19; 128/205.24; 128/205.27; 128/207.14; 128/207.15; 251/149.1

(58) Field of Classification Search ............ 128/200.26, 128/207.14, 207.15, 207.16, 205.24; 251/149.1
See application file for complete search history.

(56) References Cited

U.S. PATENT DOCUMENTS

| 4,243,034 A | | 1/1981 | Brandt | |
|---|---|---|---|---|
| 4,850,350 A | * | 7/1989 | Jackson | 128/207.16 |
| 4,960,412 A | * | 10/1990 | Fink | 604/167.04 |
| 5,255,676 A | * | 10/1993 | Russo | 128/207.14 |
| 5,269,771 A | * | 12/1993 | Thomas et al. | 604/539 |
| 5,396,925 A | | 3/1995 | Poli | |
| 5,598,840 A | | 2/1997 | Iund et al. | |
| 5,775,325 A | | 7/1998 | Russo | |
| 6,766,824 B2 | * | 7/2004 | Taylor | 137/522 |
| 6,923,184 B1 | * | 8/2005 | Russo | 128/207.14 |
| 2003/0037820 A1 | | 2/2003 | Williamson et al. | |
| 2003/0066980 A1 | * | 4/2003 | Hishikawa | 251/149.1 |
| 2006/0202146 A1 | * | 9/2006 | Doyle | 251/149.1 |

FOREIGN PATENT DOCUMENTS

| JP | 55-76659 | 6/1980 |
|---|---|---|
| JP | 11-505731 | 5/1999 |
| WO | WO 96/21476 | 7/1996 |
| WO | 96/36378 | 11/1996 |
| WO | WO 03/053271 | 7/2003 |

* cited by examiner

*Primary Examiner*—Justine R Yu
*Assistant Examiner*—Clinton Ostrup
(74) *Attorney, Agent, or Firm*—Louis Woo

(57) ABSTRACT

A closed system suction catheter has a catheter enclosed within a flexible envelope secured between a patient end fitting and a machine end fitting. The patient end fitting has a cleaning chamber with a valve at its patient side and is normally closed so that the cleaning chamber is isolated from the patient. The valve has an outer rigid housing enclosing a one-piece elastomeric moulding of tubular shape. The elastomeric moulding has two pads projecting externally through openings in the outer housing. The elastomeric moulding also has a web extending internally across its diameter with a diametrically-extending slit aligned with the pads. A collar mounted on the housing is slidable along the housing to engage the pads so as to apply pressure across the web and open the slit, thereby allowing the catheter to be advanced to the patient.

12 Claims, 2 Drawing Sheets

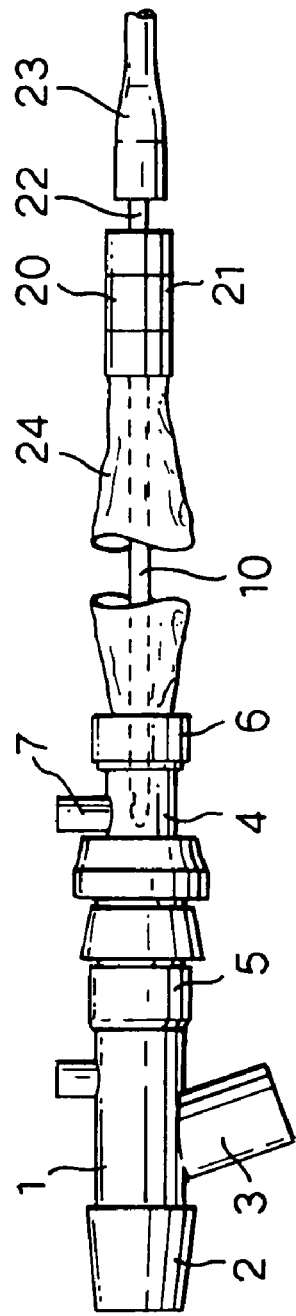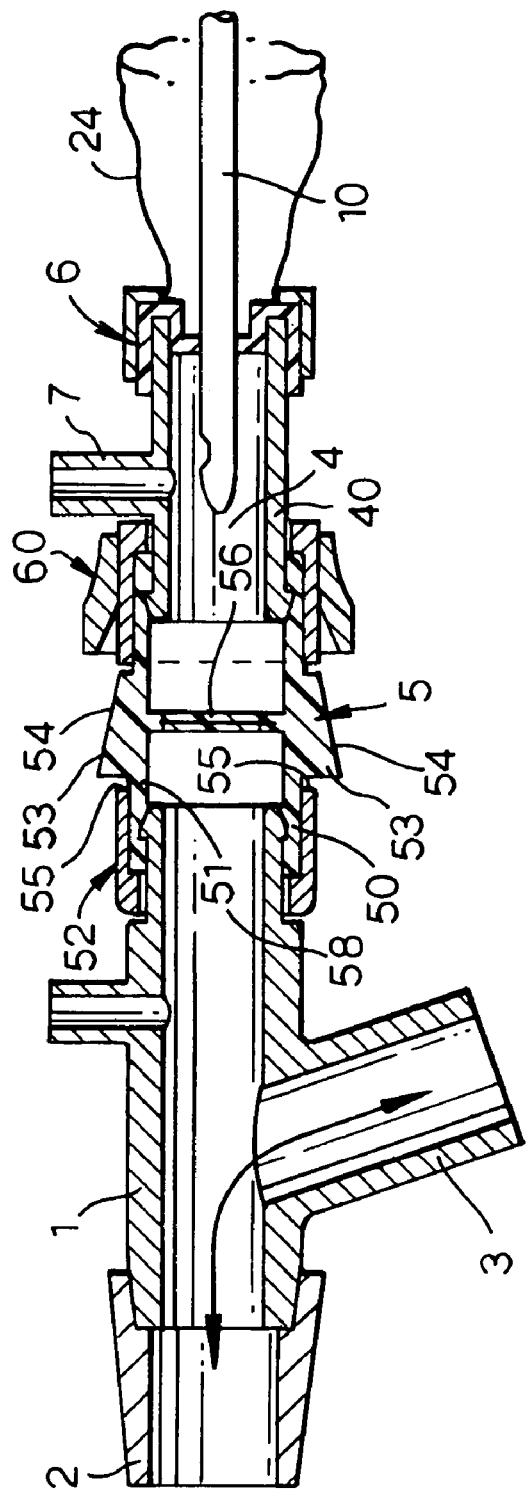

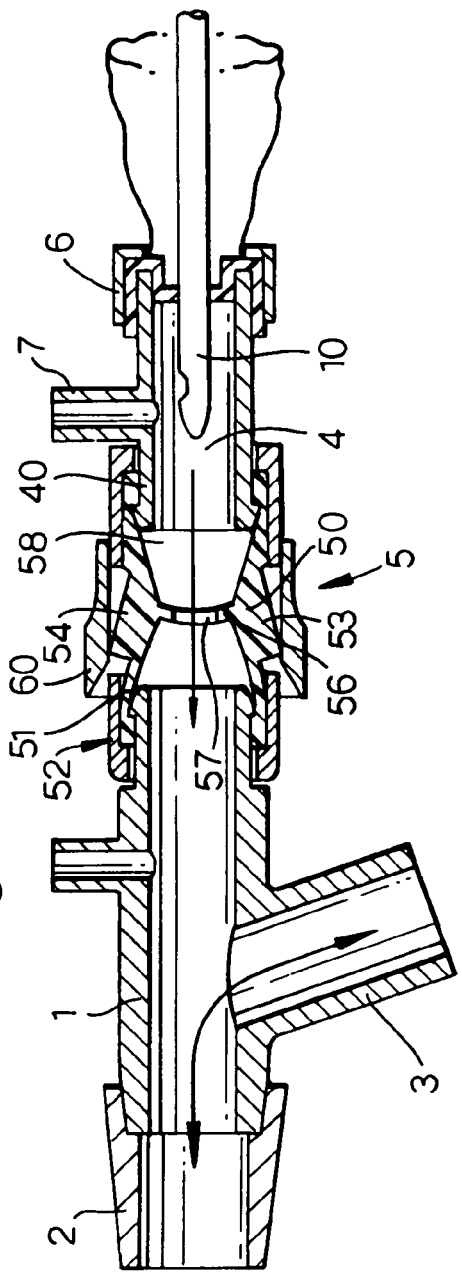
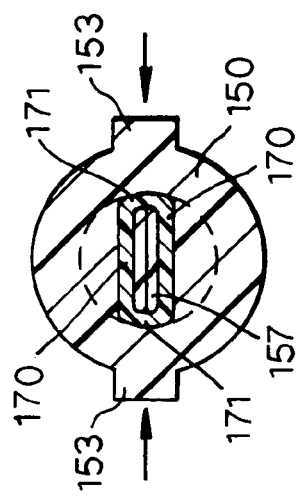
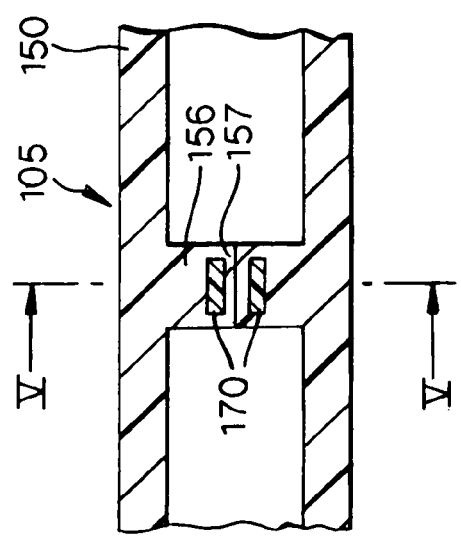

ions from within the trachea or bronchii of an intubated patient. The assembly comprises a flexible catheter connected at its machine end with a fitting including a valve that can be opened or closed to control the application of suction to the catheter. The valve is usually of a kind having a valve member movable laterally of a flow path between two positions where flow is either enabled or prevented.

VALVES

BACKGROUND OF THE INVENTION

This invention relates to valves.

Closed system suction catheter assemblies are used for removing secretions from within the trachea or bronchii of an intubated patient. The assembly comprises a flexible catheter connected at its machine end with a fitting including a valve that can be opened or closed to control the application of suction to the catheter. The valve is usually of a kind having a valve member movable laterally of a flow path between two positions where flow is either enabled or prevented.

Towards its patient end, the catheter extends through a forward, patient end fitting connected between the end of a tracheal tube and a ventilation circuit. The catheter can be advanced through the forward coupling down the tracheal tube to enable suctioning. A flexible envelope extends between the two couplings, enclosing the catheter so that it can be manipulated through the envelope. A wiper seal in the forward coupling prevents gas from the ventilation system inflating the envelope. Assemblies of this kind are sold by Portex, Inc under the trade mark STERI-CATH®, by Ballard Medical, Inc/Kimberly-Clark under the trade mark TRACH-CARE® and by Sorenson Critical Care, Inc. In some assemblies, provision is made for cleaning the catheter after its patient end has been withdrawn into the forward coupling. A manually-operable valve is located forwardly of the wiper seal providing a cleaning chamber between the valve and the wiper seal. An irrigation port opens into this chamber so that saline can be supplied to it, which is then drawn along the bore of the catheter by the applied suction to remove matter collected within the bore.

The valve used to close the washing chamber could be of various different kinds. U.S. Pat. No. 5,354,267 and U.S. Pat. No. 5,882,348 describe rotary stop-cock type valves, which are turned either to isolate the cleaning chamber from the patient end of the coupling or to enable the catheter to be advanced through the valve into the trachea. An alternative form of valve is described in U.S. Pat. No. 5,775,325. This valve is of the duck-bill type within an integral, deformable outer tube. The valve has a normally-closed slit and this is opened by squeezing the sides of the outer tube together parallel to the length of the slit. This valve has certain advantages because it can be made as an integral component. However, it also has a number of disadvantages. In particular, the valve has to be held open continuously manually while the catheter is advanced. This can be tiring in prolonged operation and means that the user has to occupy one hand maintaining the valve open. There is also a risk that the valve may not be held fully open during extension of the catheter. This could cause dragging on the catheter and may wipe secretions from the outside of the catheter in a position where they could move back into the airway. Furthermore, there is a risk that twisting or bending the assembly in the region of the cleaning chamber could inadvertently open the valve. U.S. Pat. No. 6,543,451 describes a valve opened by advancing the catheter. This valve rubs along the outside of the catheter as it is withdrawn and may also dislodge secretions.

BRIEF SUMMARY OF THE INVENTION

It is an object of the present invention to provide an alternative valve.

According to one aspect of the present invention there is provided a valve including a deformable member having a fluid passage extending therethrough, a normally-closed opening within the passage arranged such that it can be opened by external pressure applied to the deformable member, the valve including external means displaceable on the deformable member between a first position in which the opening through the deformable member remains substantially closed and a second position in which the opening is opened.

The external means is preferably arranged to remain in the first or second position until manual force is applied to displace it to the other position. The external means may be a collar embracing the deformable member and it may be displaceable by sliding lengthwise of the passage. The first position may be located to one side of the opening and the second position may be substantially aligned with the opening. The valve preferably includes a rigid housing externally of the deformable member, a part of the deformable member projecting outwardly through an opening in the rigid housing for engagement by the external means. The deformable member preferably has a part with an inclined surface arranged for engagement by the external means. The housing preferably has two openings located diametrically opposite one another, the deformable member having two parts in the form of pads projecting outwardly through respective ones of the openings, the pads each having an inclined external surface shaped for engagement by the external means such that displacement of the external means causes the pads to be pushed inwardly towards one another and the opening to be opened. The normally-closed opening may be a slit extending diametrically of the passage. The deformable member may be generally tubular, the slit being provided in a transverse web extending across the diameter of the deformable member and formed integrally with the deformable member. The valve may include a substantially rigid reinforcement member extending parallel to the slit on opposite sides such that when a force is applied externally along the slit the reinforcement member is bowed outwardly to open the slit.

According to another aspect of the present invention there is provided a valve including a deformable member having a fluid passage extending therethrough and an internal seal of a deformable material defining a slit extending transversely of the fluid passage, the seal including a substantially rigid reinforcement member extending parallel to the slit on opposite sides such that when a force is applied externally along the slit the reinforcement member is bowed outwardly to open the slit.

According to a further aspect of the present invention there is provided a closed system suction catheter assembly including a suction catheter and a valve according to the above one or other aspect of the present invention.

The assembly may include a cleaning chamber located towards the patient end of the assembly, the valve being located towards the patient side of the cleaning chamber and the valve being openable to allow extension of the suction catheter and being closable substantially to isolate the cleaning chamber from the patient and enable cleaning of the catheter. Alternatively, the valve may be located towards the machine end of the assembly and be connected at the machine end of the suction catheter so as to enable or prevent suctioning along the catheter.

A closed system suction catheter assembly according to the present invention will now be described, by way of example, with reference to the accompanying drawings.

BRIEF DESCRIPTION OF THE DRAWINGS

FIG. 1 is a simplified, side elevation view of a closed system suction catheter assembly;

FIG. 2 is a sectional side elevation view of the patient end of the assembly with the washing chamber valve closed;

FIG. 3 is a sectional side elevation view of the patient end of the assembly with the washing chamber valve open;

FIG. 4 is a sectional side elevation view of a modified form of the valve; and

FIG. 5 is a transverse sectional view along the line V-V of FIG. 4.

DETAILED DESCRIPTION OF THE PREFERRED EMBODIMENTS

With reference first to FIG. 1, the assembly comprises a patient end fitting 1 having a tapered female coupling 2 at one end adapted to fit with a male connector on the end of a tracheal tube (not shown). The fitting 1 has a side coupling 3 adapted for connection to a ventilation system. Joined with the rear end of the fitting 1 is a cleaning chamber 4 having a valve 5 at its forward end and a wiper seal 6 at its rear end. An irrigation port 7 opens into the cleaning chamber 4. The forward end of a suction catheter 10 extends slidably through the wiper seal 6 and is located rearwardly of the valve 5, when not in use. The rear end of the suction catheter 10 is fixed at a machine end fitting 20, which includes a suction control valve 21 and a spigot 22 connected to flexible tubing 23 extending to a suction source (not shown). The valve 21 has a normally closed state, where no suction is applied to the catheter 10, but can be actuated manually to open it and apply suction from the tubing 23 to the catheter. A flexible envelope 24 encloses the catheter 10 where it extends between the two fittings 1 and 20, the envelope being joined to the fittings at opposite ends.

With reference now also to FIGS. 2 and 3, the valve 5 includes a single, one-piece moulding 50 of a resilient elastomeric material having a tubular sleeve 51. The sleeve 51 extends coaxially within an outer rigid, tubular housing 52, which traps the forward end of the sleeve on the outside of the patient fitting 1. The housing 52 also traps the rear end of the sleeve 51 on the forward end of a tubular fitting 40 forming a part of the cleaning chamber 4. Midway along its length, the moulding 50 has two pads 53 diametrically opposite one another on the outer surface, the pads being square in shape and having an inclined surface 54, which increases in height in the forward direction. The two pads 53 project outwardly through two openings 55 in the housing 52. Internally, the moulding 50 has an integral, transverse web 56 extending across the diameter of the sleeve 51. The web 56 has a slit 57 through it extending diametrically between the two pads 53 across a passage 58 through the sleeve 51. In its natural state, the slit 57 is closed (as shown in FIG. 2), preventing substantial fluid flow along the passage 58. The slit 57, however, can be opened (as shown in FIG. 3) by squeezing the sleeve 51 along the length of the slit, that is, by squeezing the two pads 53 together.

The valve 5 is completed by a locking collar 60 of circular section mounted on the outside of the housing 52 to the rear, machine side of the web 56, the openings 55 and the pads 53. The collar 60 can be slid forwardly over the pads 53 to align with the web 56. In this position the inner surface of the collar 60 engages the inclined surfaces 54 on the pads 53, it pushes them inwardly and hence applies a force to squeeze the ends of the slit 57 together, thereby opening it. The collar 60 can be left in this position to keep the slit 57 open, and hence keep the valve 5 open, as long as desired, without the need for continuous manual pressure. When the valve 5 needs to be closed, the user simply slides the collar 60 rearwardly to its original position so that the resilience of the moulding 50 closes the slit 57 again. It will be appreciated that there are various other forms of external means that could be used to maintain the valve open. For example the valve could have a rotatable collar with an inner cam surface that pushes the pads in when rotated. The collar could be arranged to cooperate with a bayonet type fitting, such as an L-shape slot on the outside of the housing, so that it can be locked securely in the open position by sliding forwards and then twisting.

The suction control valve 21 in the machine end fitting 20 could be of a conventional kind or it could be of the same kind as shown in FIGS. 2 and 3. The suction control valve 21 is operable to enable or prevent suctioning along the suction catheter 10.

The arrangement of the present invention ensures that the valve is maintained fully open during use and that the suction catheter can be pushed through the valve without the catheter being squeezed between edges of the slit and scraping off material from the outside of the catheter. It also avoids the need for the user to maintain a grip on the valve during use. Because the resilient moulding is enclosed within a rigid outer housing and is accessible only through openings in the housing, there is no risk that the user could squeeze the valve too tightly and compress the valve onto the catheter. The rigid outer housing also prevents the valve being opened inadvertently by a twisting or bending action.

With reference now to FIGS. 4 and 5, there is shown an alternative form of valve 105. This has a moulding 150 similar to that of the valve 5 but differs in that the web 156 includes two semi-rigid elongate strips 170 bonded with it and extending along opposite sides of the slit 157. The two strips 170 are joined at opposite ends by respective living hinges 171. The nature of the strips 170 is such that, when the pads 153 are squeezed together along the length of the slit 157, the strips bow outwardly away from one another and hold the slit open. This arrangement provides a more positive open or closed feel to the valve and ensures that, when the valve is open, the size of the opening is always sufficient to allow free, unimpeded movement of the catheter through the opening. This form of valve could be actuated directly between the finger and thumb of the user, or it could be opened by a collar or similar external member that would maintain the valve open without the need for manual pressure.

What I claim is:

1. A closed system suction catheter assembly comprising: a machine end fitting; a patient end fitting; a suction catheter secured at one end with said machine end fitting; and a flexible envelope attached at one end with said machine end fitting and at its other end with said patient end fitting, said flexible envelope extending between the machine end fitting and the patient end fitting around the suction catheter, wherein said machine end fitting includes a suction control valve operable to control suction applied by said suction catheter, and wherein said patient end fitting includes a valve, said valve comprising: a deformable member, said deformable member having a fluid passage extending therethrough, and a normally-closed opening within said passage arranged such that it can be opened by external pressure applied to said deformable member; and an external member displaceable on and separate from said deformable member with respect to said deformable member between a first position at which said external member can be released and in which said opening through said deformable member remains substantially closed and a second position in which said opening is opened and remains open when said external member is released even in the absence of any member extending within said passage, such that, when the external member is in the second position the suction catheter can be advanced and retracted through the passage in the deformable member.

2. The assembly according to claim 1, wherein said external member is a collar embracing said deformable member.

3. The assembly according to claim 1, wherein said external member is displaceable by sliding lengthwise of said passage.

4. The assembly according to claim 1, wherein said first position is located to one side of said passage and said second position is substantially aligned with said passage.

5. The assembly according to claim 1 including a rigid housing externally of said deformable member and wherein a part of said deformable member projects outwardly through an opening in said rigid housing for engagement by said external member.

6. The assembly according to claim 5, wherein said housing has two openings located diametrically opposite one another, wherein said deformable member has two pads projecting outwardly through respective ones of said openings, and wherein said pads each have an inclined external surface shaped for engagement by said external member such that displacement of said external member causes said pads to be pushed inwardly towards one another thereby opening said opening.

7. The assembly according to claim 1, wherein said deformable member has a part with an inclined surface arranged for engagement by said external member.

8. The assembly according to claim 1, wherein said normally-closed opening is a slit extending diametrically of said passage.

9. The assembly according to claim 8, wherein said deformable member is generally tubular and has a transverse web extending across its diameter and formed integrally with said deformable member, and wherein said slit is provided in said web.

10. The assembly according to claim 8 including a substantially rigid reinforcement member extending parallel to said slit on opposite sides such that when a force is applied externally along said slit said reinforcement member is bowed outwardly to open said slit.

11. The assembly according to claim 1 including a cleaning chamber located in said patient end assembly fitting, wherein said valve is located towards a patient side of said cleaning chamber, and wherein said valve is openable to allow extension of said suction catheter and is closable substantially to isolate said cleaning chamber from the patient and enable cleaning of said catheter.

12. A closed system suction catheter assembly comprising: a suction catheter, a machine end fitting including a suction control valve arranged to control suction applied to said catheter, a patient end fitting having a sliding seal through which said suction catheter can be advanced and retracted, and a flexible envelope extending between said machine end fitting and said patient end fitting and enclosing said catheter between said fittings, wherein said patient end fitting includes a cleaning chamber on a patient side of said sliding seal, said cleaning chamber including an inlet for cleaning fluid and a valve, and wherein said valve includes a tubular deformable member, said deformable member having a fluid passage extending therethrough, a closure member extending across said fluid passage and having a slit normally closed to isolate said cleaning chamber from the patient; and an external collar slidable along said tubular member with respect to said tubular member between a first position in which said slit remains substantially closed when the collar is released and a second position in which said collar applies pressure to said tubular member to open said slit and said slit remains open when the collar is released to allow the catheter to be advanced from and retracted to said cleaning chamber even in the absence of any member extending within said passage.

* * * * *